(12) United States Patent
Lee et al.

(10) Patent No.: US 8,715,739 B2
(45) Date of Patent: May 6, 2014

(54) POLYMER COATED MICROPARTICLES

(75) Inventors: Gil U. Lee, West Lafayette, IN (US);
Hao Shang, West Lafayette, IN (US);
Won-Suk Chang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 2065 days.

(21) Appl. No.: 11/552,324

(22) Filed: Oct. 24, 2006

(65) Prior Publication Data

US 2007/0172426 A1    Jul. 26, 2007

Related U.S. Application Data

(60) Provisional application No. 60/729,769, filed on Oct. 24, 2005.

(51) Int. Cl.
*A61K 9/50* (2006.01)

(52) U.S. Cl.
USPC ........... 424/490; 424/489; 424/493; 424/496; 424/501

(58) Field of Classification Search
USPC ................................ 424/489–501
See application file for complete search history.

(56) References Cited

U.S. PATENT DOCUMENTS

| | | | |
|---|---|---|---|
| 4,230,685 A | | 10/1980 | Senyei et al. |
| 4,438,239 A | * | 3/1984 | Rembaum et al. ........... 525/54.1 |
| 4,654,267 A | | 3/1987 | Ugelstad et al. |
| 4,695,392 A | | 9/1987 | Whitehead et al. |
| 5,232,782 A | | 8/1993 | Charmot |
| 5,236,824 A | | 8/1993 | Fujiwara et al. |
| 5,538,739 A | | 7/1996 | Bodmer |
| 5,648,124 A | * | 7/1997 | Sutor ........................... 427/475 |
| 5,814,687 A | | 9/1998 | Kasai et al. |
| 5,846,517 A | | 12/1998 | Unger |
| 5,938,581 A | | 8/1999 | Bibette et al. |
| 6,133,047 A | | 10/2000 | Elaissari et al. |
| 6,180,418 B1 | | 1/2001 | Lee |
| 6,245,483 B1 | * | 6/2001 | Oshimo et al. ............. 430/281.1 |
| 6,294,342 B1 | | 9/2001 | Rohr et al. |
| 6,866,838 B1 | | 3/2005 | Mondain-Monval et al. |
| 6,878,445 B2 | | 4/2005 | Hattori et al. |
| 2003/0199653 A1 | | 10/2003 | McCormick, III |
| 2005/0042192 A1 | * | 2/2005 | Evans et al. ................ 424/70.11 |

OTHER PUBLICATIONS

Enhancement by N-Hydroxysulfosuccinimide of Water-Soluble Carbodimide-Mediated Coupling Reactions—James v. Staros, Rick W. Wright, and Deborah M. Swingle—Analytical Biochemistry 156, 220-222 (1986).
Zero-Length Crosslinking Procedure with the Use of Active Esters—Zenon Grabarek and John Gergely—Analytical Biochemistry 185, 131-135 (1990).
Novel crosslinking methods to design hydrogels—W.E. Hennink, C.V. van Nostrum—Advanced Drug Delivery Reviews 54 (2002) 13-16.
Hao Shang & Gil U Lee, Preparation of Monodisperse Magnetic Particles Through Membrane Self-assembly, Annual Meeting of the AIChE (Nov. 7-12, 2004), Abstract.
Hao Shang & Gil U Lee, Preparation of Monodispersed Magnetic Microparticles Using Templated Self-Assembly, American Filtration and Separations Society (Apr. 10-13, 2005), Abst.

* cited by examiner

*Primary Examiner* — Michael G Hartley
*Assistant Examiner* — Micah-Paul Young
(74) *Attorney, Agent, or Firm* — Lowe Hauptman & Ham, LLP

(57) ABSTRACT

Methods for preparing uniformly sized micropanicles, with an optional polymeric coating generally include: 1) providing nanoparticles, preferably having a size of between 1 nm and 100 nm; 2) adding a hydrophobic surface layer to the nanoparticles; 3) making a suspension of the hydrophobic nanoparticles and a polymerization initiator in an hydrophobic solvent; 4) dissolving a monomer in the hydrophobic solvent; 5) making an emulsion by dispersing droplets of the hydrophobic solvent in a continuous aqueous phase with an emulsifier; 6) sizing the first emulsion to provide a second emulsion of the same components in which the droplets are substantially uniform and between 2 and 20 um in size; 7) evaporating at least a substantial portion of the dispersed hydrophobic droplets to assemble nanoparticles to form micropanicles suspended now in the aqueous phase; 8) replacing the first surfactant with a second surfactant, which is preferably a polymerizable surfactant; 9) adding a polymerizable monomer to the aqueous phase and allowing it to adsorb into the microparticle; 10) polymerizing the monomer(s) to provide a polymer layer on the micropanicles; and 11) functionalizing the polymer surface layer erf the micropanicles with one or more polymer, nanoparticle or biological macromolecular layers.

33 Claims, 12 Drawing Sheets

POLYMER COATED MICROPARTICLES

REFERENCE TO RELATED APPLICATIONS

This application claims the benefit of U.S. Provisional Patent Application 60/729,769, filed Oct. 24, 2005, which is hereby incorporated by reference.

FIELD OF THE INVENTION

The present invention relates generally to methods for producing uniform micrometer-sized particles comprising densely packed nanoparticles, and more particularly to methods for making highly uniform, high magnetic moment, polymer coated, magnetic microparticles using an emulsion based-templated assembly technique. Such particles are useful in bioseparations, biophysical measurements, bioanalytical assays, drug delivery, hyperthermia treatment and magnetic resonance imaging (MRI).

DESCRIPTION OF THE RELATED ART

Polymer-coated paramagnetic microparticles have been employed in a variety of applications, such as bioseparations, biophysical measurements, bioanalytical assays, therapeutics, and MRI. Magnetic particles can be coated with specific chemistries such that the particles have the ability to bind the corresponding targets from a mixture of biological materials. These magnetic particles can be separated from the mixture by being attracted to an external magnetic field such that the target bound to the particle surface can be separated. The ability to bind specific biological materials to the magnetic particles provides a simple and effective means for the separation and purification of cells, viruses, and biological macromolecules. Examples of relevant peer reviewed publications include Kemshead et al, "Monoclonal-Antibodies Attached to Microspheres Containing Magnetic Compounds, Used to Remove Neuro-Blastoma Cells from Bone-Marrow Taken for Autologous Transplantation," European Journal of Cancer & Clinical Oncology, 18(10), 1982, pp1043; Dirami et al, "Separation and Characterization of Leydig Cells and Macrophages from Rat Testes", Journal of Endocrinology, 130(3), 1991, pp357-365; Ahmed et al, "Isolation and Partial-Purification of a Melanocyte-Stimulating Hormone Receptor from B16 Murine Melanoma-Cells—a Novel-Approach Using a Cleavable Biotinylated Photoactivated Ligand and Streptavidin-Coated Magnetic Beads", Biochemical Journal, 286, 1992, pp377-382; Ito et al, "Sequence-Specific DNA Purification by Triplex Affinity Capture", Proceedings of the National Academy of Sciences of the United States of America, 89(2), 1992, pp495-498; McCornell et al, "Biopanning phage display libraries using magnetic beads vs. polystyrene plates", Biotechniques, 26(2), pp208. Examples of relevant patents include U.S. Pat. Nos. 4,695,392 and 4,230,685.

Magnetic particles have also been employed as a tool in biophysical measurements. The ability of generating a force under a magnetic field has made the particles particularly useful in biological science to characterize specific binding interactions and to differentiate specific and nonspecific binding interactions. The use of magnetic particles in biophysical measurements is described, for example, in Shang et al, "The Application of Magnetic Force Differentiation for the Measurement of the Affinity of Peptide Libraries", Journal of Magnetism and Magnetic Materials, 293, 2005, pp382-388; Strick et al, "The elasticity of a single supercoiled DNA molecule", Science, 271(5257), 1996, 1835-1837.

Magnetic particles have been utilized as a bioanalytical tool. U.S. Pat. No. 5,236,824 describes an in-situ laser magnetic immunoassay method, which permits a quantitative determination of a target immunological substance in an analyte solution containing both bound and free species. The force discrimination assay is described in U.S. Pat. No. 6,180,418 B1. U.S. Pat. No. 6,294,342 B1 describes assay methods utilizing the response of magnetic particles to the influence of a magnetic field to qualitatively or quantitatively measure binding between specific binding pairs and hence the presence or amount of analyte contained in a test sample can be determined.

Magnetic particles have been utilized in medical research, especially in drug delivery, hyperthermia treatment and MRI imaging. Magnetic particles have been used to carrier and localize the therapeutic agent to a specific target as described in Yellen et al, "Targeted drug delivery to magnetic implants for therapeutic applications", Journal of Magnetism and Magnetic Materials, 293 (1), 2005, pp647-654; Saravanan et al, "Ultrasonically controlled release and targeted delivery of diclofenac sodium via gelatin magnetic microspheres", International Journal of Pharmaceutics, 283(1-2), 2004, pp71-82. In hyperthermia treatment the heat generated by the magnetic particles under a AC field is used to kill malfunctional cells, such as cancer, as presented in Uskokovic et al, "Silica-coated lanthanum-strontium manganites for hyperthermia treatments", Materials Letters, 60(21-22), 2006, pp2620-2622; Jordan et al, "The effect of thermotherapy using magnetic nanoparticles on rat malignant glioma", Journal of Neuro-Oncology, 78(1), 2006, pp7-14. Magnetic particles, as a contrast agent, can enhance the performance of MRI image. Numerous research has been done in this area, such as Dousset et al, "MR Imaging of relapsing multiple sclerosis patients using ultra-small-particle iron oxide and compared with gadolinium", American Journal of Neuroradiology, 27(5), 2006, pp1000-1005; McDonald et al, "Investigations into the physicochemical properties of dextran small particulate gadolinium oxide nanoparticles", Academic Radiology, 13(4), 2006, pp421-427; Kleinschnitz et al, "In vivo detection of developing vessel occlusion in photothrombotic ischemic brain lesions in the rat by iron particle enhanced MRI", Journal of Cerebral Blood Flow and Metabolism, 25(11), 2005, pp1548-1555.

These applications require magnetic particles that are micrometer in size, stable in physiological salt solutions, and have a high and uniform magnetization with little residual magnetization.

U.S. Pat. No. 4,654,267 describes possibly the first magnetic particle in which the magnetic polymer particles were prepared by treating compact or porous polymer particles with a solution of iron salts, which can form nanometer size iron oxide particles by raising the pH value. At least three other methods have been developed to produce magnetic microparticles. First, In core-shell processing nanometer scale magnetic particles are physically or chemically adsorbed onto a polymer particle of micron size as described in Bizdoaca et al, "Magnetically directed self-assembly of submicron spheres with a Fe3O4 nanoparticle shell", Journal of Magnetism and Magnetic Materials, 240(1-3), 2002, pp44-46. U.S. Pat. No. 6,133,047 describes the superparamagnetic particles comprised a core of a first polymer, an internal layer of a second polymer coating the core in which a magnetic material is distribute, and an external layer of a third polymer coating the magnetic layer. U.S. Pat. No. 5,232,782 describes a procedure to make magnetizable core-shell microparticles based a cross-linked organopolysiloxane. The second approach uses heterogeneous polymerization of nanosize magnetic particles and a polymer monomer as described in Rana et al, "Synthesis of magnetic beads for solid phase synthesis and reaction scavenging", 40(46), 1999, pp8137-8140. In the third approach, emulsion techniques are used to synthesize the microparticles. U.S. Pat. No. 5,814,687 describes a method to produce magnetic polymer particles by dispersing the nanomagnetic particles in hydrophobic monomer solution with the hydrophobic initiator. An emulsion was prepared by dispersing the monomer solution in water and polymerization was initiated by heating.

SUMMARY OF THE INVENTION

The present invention relates generally to methods for producing uniform micrometer-sized particles comprising densely packed nanoparticles, and more particularly to methods for making highly uniform, high magnetic moment, polymer coated, magnetic particles. One preferred aspect of the invention comprises: 1) providing nanoparticles, preferably having a size of between 1 nm and 100 nm; 2) optionally adding a hydrophobic surface layer to the nanoparticles; 3) making a suspension of the hydrophobic nanoparticles and polymerization initiator in a hydrophobic solvent; 4) optionally dissolving a monomer in the hydrophobic solvent; 5) making an emulsion by dispersing droplets of the hydrophobic solvent in a continuous aqueous phase with an emulsifier; 6) optionally sizing the first emulsion to provide a second emulsion of the same basic components but in which the droplets are substantially uniform and between 2 and 20 μm in size; 7) evaporating at least a substantial portion of the dispersed hydrophobic droplets to assemble nanoparticles to form microparticles suspended now in the aqueous phase; 8) optionally replacing the first surfactant with a second surfactant, which is preferably a polymerizable surfactant; 9) optionally adding a polymerizable monomer to the aqueous phase and allowing it to adsorb into the microparticle; 10) polymerizing the monomer(s) to provide a polymer layer on the microparticles; and 11) optionally functionalizing the polymer surface layer of the microparticles with one or more polymer, nanoparticle or biological macromolecular layers.

Another aspect of the present invention provides a similar method wherein hydrophilic nanoparticles are dispersed in an aqueous phase suspended in a continuous hydrophobic phase, which is commonly known as a water-in-oil emulsion. In this method the initiator should be soluble in the aqueous phase. The hydrophobic phase must be selected to have a lower vapor pressure than the aqueous phase so that the aqueous phase may be evaporated to allow assembly of the nanoparticles.

The preferred microparticles have a polymeric coating and a magnetic content that comprises in excess of 50%, preferably in excess of 70%, and more preferably in excess of 90%, of the particle's mass. The polymeric shell may contain one or more functional groups capable of forming covalent bonds useful in managing a variety of separations.

One benefit of the present invention is the ability to provide magnetically responsive microparticles having a core comprising nanoparticles which are superparamagnetic and exhibit negligible residual magnetism. Such nanoparticles may be made of magnetite, may be less than 50 nm in size, and may exhibit only paramagnetic properties.

Another benefit of the present invention is the production of a magnetic microparticle with uniform magnetization. Uniform magnetization is promoted by producing uniformly dispersed nanoparticles in hydrophobic solvent as disclosed above.

Another benefit of the present invention is to provide magnetic microparticles whose overall diameter can be varied within a wide range by simply changing the loading of nanoparticles or emulsion size. The assembled microparticles preferably range in size from 0.01 to 5 microns in diameter. In some embodiments the particles range in size from 0.1 to 3.0 microns, while in other embodiments the particles range in size from 0.5 to 2.0 microns in diameter.

Another benefit of the present invention is the development of a magnetic microparticle whose size distribution can be controlled in a narrow range. With the disclosed materials and methods the sizes of the assembled microparticles can be controlled such that the microparticles are uniform in size, with a coefficient of variance (of particle size) of less than 40%, preferably less than 20%, more preferably less than 5%, and most preferably less than 2% being obtainable for batches of microparticles made by the disclosed method.

Another benefit of the present invention is to provide the polymerization process in which the initiator is confined within and on the surface of the core particles without leaking into the solutions in which the particles are suspended. With the methods of the present invention the polymerization only happens within and around the surface of the particles because this is where the initiator is. This is in contrast to methods in which the initiator is allowed to leak into the solution, causing the whole solution to be polymerized and making the particles aggregate together.

Another benefit of the present invention is to provide the particles with functional groups, such as carboxyl and primary amine, so that the particles are stable in physiological salt solutions and biomolecules of interest can be covalent attached to the particle surface.

Another benefit of the present invention is to provide methods for forming particles coated with a layer of poly(ethylene glycol) or other hydrophilic polymer such as dextran, which may be used to reduce the nonspecific adsorption of proteins to the particle surface.

Another benefit of the present invention is to provide methods for forming particles coated with a layer of nanoparticles, which may be used to impart specific properties or functional behavior to the microparticle.

Another benefit of the present invention is to provide magnetic particles with the polymer coating that can suppress the nonspecific adsorption and react specifically to the target so that the false positive is minimized.

The novel coated magnetic particles prepared by the methods described above and illustrated below have magnetic "core" (i.e., the bare nanoparticles without their hydrophobic or hydrophilic coatings, and without a polymer coating) that comprises a significant proportion of the particle's mass. Preferred coated particles have a magnetic core that comprises in excess of 50%, preferably in excess of 70%, more preferably in excess of 80%, and most preferably in excess of 90%, of the particle's mass. This is in contrast to prior art method in which the core typically comprises 10-30% of the particle mass. The larger magnetic core may result in increased magnetization for the finished particles. For example, some aspects of the present invention provide coated microparticles having magnetization as high as about 25 to about 50 emu/g.

In another aspect of the invention the particles have both a bare nanoparticle core in excess of 70% of the particle's mass, and a coefficient of variance (of particle size) of less than 40%. Preferred particles have both a bare nanoparticle core in excess of 80% of the particle's mass, and a coefficient of variance (of particle size) of less than 20%, while more preferred particles have both a bare nanoparticle core in excess of 80% of the particle's mass, and a coefficient of variance (of particle size) of less than 5%.

Other preferred microparticles may have a core comprising more than one type of nanoparticle. That is, diverse nanoparticles may be assembled into homogeneous cores if they are similar size and surface energy.

DETAILED DESCRIPTION OF THE INVENTION

For the purposes of promoting an understanding of the principles of the invention, reference will now be made to specific embodiments and specific language will be used to describe the same. It will nevertheless be understood that no limitation of the scope of the invention is thereby intended. Any alterations and modifications in the described invention, and any further applications of the principles of the invention as illustrated therein are contemplated as would normally occur to one skilled in the art to which the invention relates.

Figure 1:
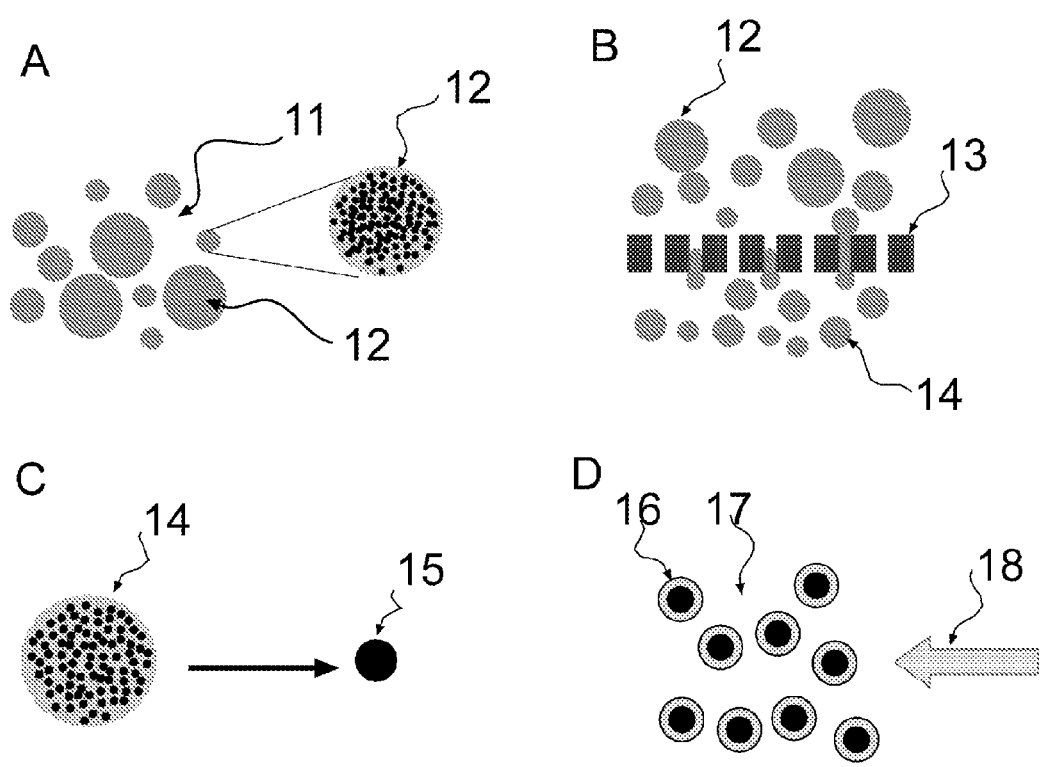
FIG. 1 illustrates one aspect of the present invention according to one preferred embodiment.

As summarized above, one aspect of the invention relates to a method for preparing microparticles with an optional polymeric coating. In one preferred embodiment the method comprises: 1) providing nanoparticles of a superparamagnetic material, preferably having a size of between 1 nm and 100 nm; 2) optionally adding a hydrophobic surface layer to the particles, preferably by combining them with a material having a first end that adsorbs to the surface of the nanoparticle and a second end that extends away from the nanoparticle and imparts hydrophobicity to the particles; 3) making a suspension of the hydrophobic nanoparticles and a polymerization initiator in the hydrophobic solvent; 4) optionally adding a polymerizable monomer to the hydrophobic solvent; 5) making an emulsion of the hydrophobic phase in an continuous aqueous phase with an emulsifier, wherein the hydrophobic phase comprises droplets in which polymerization initiator, hydrophobic nanoparticles, and optionally polymer monomer are dissolved therein, and the aqueous phase optionally comprises a viscoelastic additive; 6) optionally sizing the first emulsion to provide a second emulsion of the same basic components but in which the droplets are substantially uniformly between 2 and 20 µm in size; 7) evaporating at least a substantial portion of the hydrophobic solvent to assemble nanoparticles suspended in the hydrophobic solvent to form micron size aggregates; 8) optionally replacing the first surfactant with a second surfactant, which is preferably a polymerizable surfactant; 9) optionally adding at least one polymerizable monomer to the aqueous medium; 10) polymerizing the monomer(s) to provide a polymer layer on the microparticles; and 11) optionally functionalizing the polymer layer of the microparticles with one or more polymer, nanoparticle, or biological macromolecular layers. FIG. 1 illustrates this preferred method.

FIG. 1 illustrates certain aspects of the preferred process to produce the inventive particles. In step A the nanoparticles are suspended in hexane 12, in which benzophenone is dissolved. A crude oil-in-water emulsion is formed by dispersing the hexane solution 12 in SDS solution 11. In step B, the crude emulsion is pushed through a membrane 13 with defined pore size to form refined emulsion 14. In step C, the hexane in the refined emulsion is allowed to evaporate to form microparticles 15. In step D, the microparticles are suspended in monomer solution 17 and the polymerization is initiated by exposing the solution to UV light source 18. A polymer shell is formed around each particle 16.

The Nanoparticles.

A variety of nanoparticles known to the art can be assembled and coated by the method according to the present invention, with the preferred nanoparticles being superparamagnetic. While a variety of methods are known for forming such superparamagnetic nanoparticles, preferred magnetic nanoparticles for use in the present invention can be prepared by the co-precipitation of ferric and ferrous salts according to the method described by Landfester, "Magnetic Polystyrene Nanoparticles with a High Magnetite Content Obtained by Miniemulsion Processes", Macromolecular Chemistry and Physics, 204, 2003, pp22-31 and by U.S. Pat. No. 5,648,124. A mixture of ferrous chloride and ferric chloride in deoxygenated water is combined with aqueous ammonium hydroxide and heated with vigorous stirring. The resulting black slurry is then dialyzed, filtered, and hydrophobized with oleic acid (as described more fully below).

As indicated above, in some embodiments of the invention the nanoparticles are made from one or more magnetic materials. Accordingly, the nanoparticles may include or consist essentially of a magnetic material such as Fe (including magnetite and maghemite), Ni, and Co, or mixtures of these materials. In other embodiments magnetic alloys, such as alloys containing Mn, and/or antimony, may be used.

In other embodiments, at least some of the nanoparticles are made with one or more metallic materials. Accordingly, the nanoparticles may include or consist essentially of alumina, aluminum, magnesium, copper, silver, or gold.

In other embodiments, at least some of the nanoparticles are made with one or more nonmetallic materials. Accordingly, the nanoparticles may include or consist essentially of a powder of oxides such as silica.

The nanoparticles are preferably spherical and monodisperse. The size of the nanoparticles is preferably in the range of 1 nm to 100 nm, more preferably from 5 nm to 50 nm.

The Nanoparticle Surface Layer

The nanoparticles may be provided with a surface layer about the particle to control their surface energy and thus their solubility in either the hydrophobic or hydrophilic phases. When a hydrophobic surface layer is to be provided on hydrophilic nanoparticles this may be done, for example, by contacting the particles with a generally aliphatic compound having a polar end-group. The first end of each molecule of the compound may include a carboxyl group, an amine group, a silane, etc., that adsorbs to the surface of the particle. The second end of each molecule of the compound may include alkane group that extends away from the particle and provides hydrophobicity to the coated particle.

A wide variety of materials may be used to provide the hydrophobic surface layer. For example, saturated fatty acids such as lauric acid, myristic acid, palmitic acid, and stearic acid, and unsaturated variants thereof, such as palmitoleic acid, oleic acid, linoleic acid, and linolenic acid, may generally be used. Oleic acid has been preferred as the hydrophobic coating material in testing to date. Silanes such as octadecyl trichlorosilane have also been widely used to functionalize oxide surfaces.

The hydrophobic surface layer is generally provided simply by mixing the nanoparticles into a volume of hydrophobic coating material suitable for coating the particles. An excess of hydrophobic coating material is generally used so that the nanoparticles form a suspension in the hydrophobic coating material. Each nanoparticle will then have a hydrophobic layer on its surface.

In other embodiments, it may be desirable to suspend a hydrophobic particle in the aqueous solution. This can be done by contacting the particles with a generally aliphatic compound having a polar end-group. The hydrophobic alkane end on the molecule will adsorb on the surface of the particle leaving the hydrophilic end of the compound extending away from the particle providing a hydrophilic coat.

Formation of the Emulsion

In the present invention, an emulsion is used to facilitate assembly of the microparticles. Emulsions are formed from two immiscible phases and are stabilized through the use of emulsifiers. When the nanoparticles are suspended in a hydrophobic phase, an oil-in-water emulsion may be prepared by adding a sufficient quantity of an aqueous solution containing surfactant to the hydrophobic phase and vigorously stirring the mixture to produce a polydispersed hydrophobic phase in the continuous aqueous phase. When the nanoparticles are suspended in a hydrophilic phase, a water-in oil emulsion may be prepared by adding a sufficient quantity of a hydrophobic solution containing surfactant to the hydrophilic phase and vigorously stirring the mixture to produce a polydispersed hydrophilic phase in the continuous hydrophobic phase.

A variety of hydrophobic fluids may be used for the hydrophobic phase, including, but not limited to, alkane, alkene, cycloalkane, aromatic and non-polar organic solvents, for example, hexane, octane, cyclohexane, toluene, benzene, xylene, styrene, acrylate compounds etc. Hexane is the preferred hydrophobic phase as it has a low enough vapor pressure at room temperature that the emulsion can be processed, but the hexane can easily removed by evaporation.

The hydrophobic phase also may provide a vehicle for adding polymerization initiator and monomer to the assembled microparticles. The preferred initiators are ones that can be activated by UV light, such as benzophenone derivatives, thioxanthone derivatives, phenyl propane-one derivatives, acetophenone derivatives, phenyl ketone derivatives, phosphineoxide derivatives. UV initiator synergist such as aminobenzoate derivatives and benzoyl benzoate may be used with UV photoinitiators for more effective UV reaction. Benzophenone has been the preferred initiator in testing to date. In the preferred embodiments the polymerization initiator is soluble in the hydrophobic phase, and is added by dissolving the initiator in the hydrophobic phase. The amount of polymerization initiator is selected according to the monomers used, the amount of monomer to be polymerized and other parameters as known to those skilled in the art.

Other polymerization initiators, such as initiators that can be activated by mild heating may also be suitable. As a general rule, heat-activated initiators should allow the polymerization temperatures to remain at or below about 75° C. Examples of suitable heat activated initiators include, but are not limited to VAZO 33 (2,2'-azobis(4-methoxy-2,4-dimethylvaleronitrile) or VAZO 52 (2.2'-azo-bis(2,4-dimethylpentanenitrile), both marketed by the E.I. DuPont de Nemours & Co., Inc., Wilmington, Del.

It may be desirable to add polymer monomer to the hydrophobic phase if these monomers are sparingly soluble in the aqueous phase. Hydrophobic monomers that are soluble in the hydrophobic phase include styrene, acrylate derivatives (methylmethacrylate, methyl acrylate, ethylacrylate, hydroxyethyl acrylate, etc), maleimide and maleic anhydride monomer derivatives, vinyl monomer derivatives, etc.

Optionally, hydrophobic cross-linkers can be added to the hydrophobic solvent such as multi-vinyl compound derivatives (e.g., divinylbenzene), mutli-acrylate derivatives (e.g. methylenebis diacrylate), urethane multi-acrylate (e.g. urethane diacrylate, urethane triacrylate), pentaerythritol derivatives, polyethylene multi-acrylate (e.g. polyethylene tetraacrylate), epoxy multi-acrylate derivatives (e.g., epoxy dimethacrylate), etc.

In the preferred embodiments, the aqueous phase is an aqueous solution of a surfactant such as sodium dodecyl sulfate (SDS), Triton or Tween, with SDS being most preferred in testing to date. The surfactant stabilize the emulsion, dispersing the phase in which the surfactant does not dissolve and promoting uniform particle size and effectively stabilize the microparticles.

Emulsion Size Control.

The initial emulsions comprise a discontinuous phase with a high degree of polydispersity. One benefit of controlling the size of the particles in the emulsion is that the finished particle size can be controlled and the particle size can be made more uniform.

In one aspect of the invention, the size distribution of the discontinuous phase in the emulsion is controlled by filtration. This may be done, for example, by passing the emulsion through a membrane having a desired pore size. If the pore size of the membrane that is smaller than the average drop size of in emulsion it appears that uniform droplets are formed that are determined by the pore size the membrane, filtration pressure, and surface tension of surfactant-oil-water interface. In one preferred embodiment the membrane may have a pore size of 1 µm to 10 µm, more preferably 2 µm to 5 µm In another aspect of the invention, the size of the discontinuous phase in the emulsion was controlled using shear stress.

Figure 2:
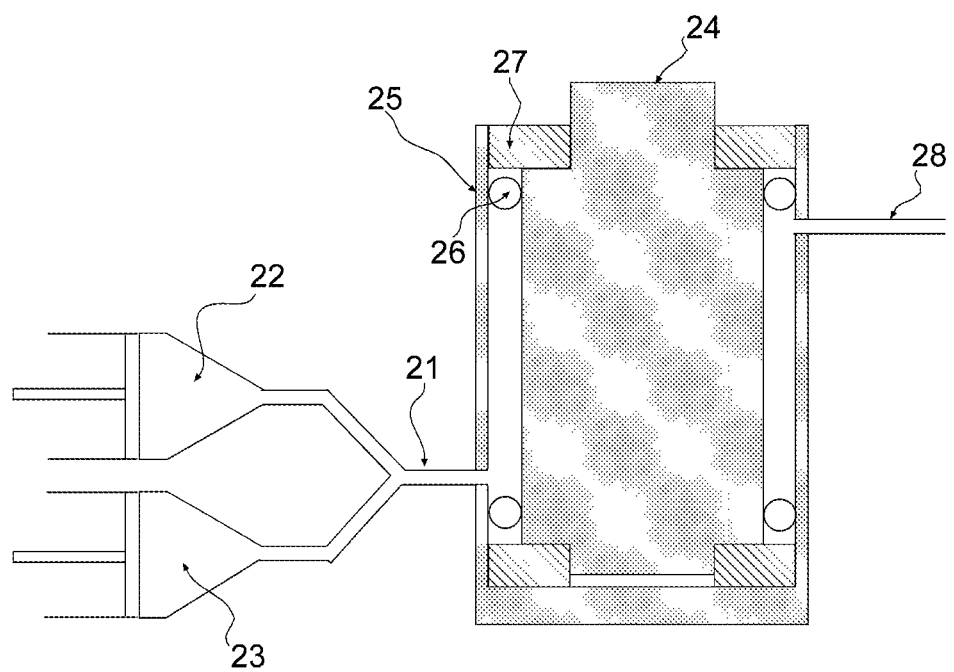
FIG. 2 shows the use of a shear device used to form emulsions.

FIG. 2 illustrates the shear device used to size of the emulsion, in which the hexane 22, which contains nanoparticles, initiators and optional hydrophobic monomers, and the aqueous solution 23 are continuously fed to the shear device through the lower port 21. The two solutions are fed directly into the shear device without preforming the emulsion. The shear device consists of two concentric cylinders 24 and 25 with a uniform gap between them. The outer cylinder 25 is immobile whereas the inner cylinder 24 rotates relative to the central axle. The gap between the inner cylinder and the outer cylinder is preferred in the range of 0.05-1 mm, more preferably 0.1 -0.3 mm. Two O-rings 26 are placed at the upper and lower ends of the inner cylinder. Two bearings 27 are placed at the upper and lower ends of the outer cylinder. The diameters of the inner and outer cylinders remain constant in the range between the two bearings. The solutions are preferred to be fed through the lower port and the emulsion is collected through the upper port 28. In such a device, the solution experiences the constant and uniform shear rate. The shear rate is controlled by an electric motor, which drives the inner cylinder. The rotation speed is monitored by a tachometer.

It is essential for the starting aqueous solution to be viscoelastic. The viscoelasticity of the aqueous solution can be obtained by incorporating one or more additives, such as dextran derivatives, sucrose derivatives, cellulose derivatives, carboxymethylcellulose derivatives, chitosan derivatives. Dextran has been the preferred additive in testing to date.

Formation of Nanoparticle Aggregates

Evaporation of the hydrophobic solvent in the emulsion gives an aqueous suspension of generally monodisperse microparticles in the form of aggregates of nanoparticles having a hydrophobic surface layer. The microparticle can be 0.01 to 5 microns in diameter, more preferably from 0.1 to 3.0 microns, and most preferably from 0.5 to 2.0 microns in diameter. Gasses such as air bubbles can be introduced to the solution to accelerate the evaporation. Preferably inert gasses are used.

Surfactant Exchange

If desired, the surfactant used when forming the emulsion can be removed from the suspension and replaced with another surfactant that has properties better suited for facilitating polymerization of the final particles. In one embodiment the first surfactant is removed by washing with an aqueous solution containing a polymerizable surfactant such as nonylphenoxypropenyl polyethylate alcohol (RN-10).

Adsorption of Monomers on the Microparticles

The microparticles may be coated with a polymer layer by addition of a polymer monomer to the aqueous solution. Monomers may include acrylic acid, methacrylic acid, fumaric acid, maleic acid, itaconic acid, vinyl acetic acid, 4-pentenoic acid, undecylenic acid, and salts thereof. Basic monomers such as acrylamide, aminoethylmethacylate, dimethylaminoethyl methacrylate, t-butylaminoethyl methacrylate, pyrrole, N-vinyl carbazole, vinylpyridine, vinylpyrrolidone and salts thereof, may generally be used. Acrylic acid has been the preferred monomer in testing to date.

A variety of co-monomers can be utilized. One particularly suitable co-monomer is RN-10, as mentioned above. Other suitable co-monomers can include difunctional monomers, such as for example di- and tri-acrylate esters of diols and triols.

When acrylic acid is used, the pH of the acrylic acid solution is preferably adjusted to 3.1 using sodium hydroxide. Testing has shown the optimal pH is in the range of 2.8-3.3.

When an initiator such as benzophenone is used, initiation involves exposing the mixture to an ultraviolet light source. The choice of ultraviolet light source depends on the initiator used, the amount of reaction volume and other parameters as known to those skilled in the art. Once the desired polymerization has been accomplished, the coated magnetic particles can be collected with a permanent magnet by diluting the viscous reaction mixture with methanol, rinsing with additional methanol and water and storing at reduced temperatures. Example 1 below illustrates preferred aspects of the present invention.

Functionalizing the Polymer Layer.

As indicated above, the polymer coating of the particles may have one or more functional groups that can bond with a variety of bioactive materials or that can be further functionalized to enable this bonding. For example, carboxylic acids attached to the coating's surface can be reacted with 1-ethyl-3-(3-dimethylaminopropyl)-carbodiimide hydrochloride (EDAC) to facilitate bonding to proteins and other bioactive materials.

In some aspects of the present invention the coating of the microparticles may have poly(ethylene glycol) functionality. This may be provided by incorporation of a co-monomer monomer such as RN-10 that minimizes non-specific absorption by the steric hindrance mechanism. Example 13 below illustrates the ability of preferred coated microparticles to absorb a target bioactive material while avoiding the absorption of a second non-target bioactive material.

Preparation of Microparticles from Water-in-Oil Emulsions

In most of the embodiments described above, the nanoparticles are suspended in a hydrophobic phase and droplets of that hydrophobic phase are then dispersed in a continuous aqueous phase. In other embodiments of the present invention it may be desirable to suspend hydrophilic nanoparticles in a hydrophilic phase and form droplets of that hydrophilic phase in a continuous hydrophobic phase. It is to be appreciated that when the water-in-oil emulsion technique is used, monomers, cross-linkers, and initiators that are soluble in the aqueous phase may be incorporated directly into the aqueous phase. In this case, the hydrophobic phase must have a low enough vapor pressure that losses are negligible during the evaporation of the hydrophilic phase.

Accordingly, one general aspect of the invention provides a method of preparing uniform microparticles, comprising:
(a) providing starting nanoparticles having either a hydrophobic surface or a hydrophilic surface, wherein said nanoparticles have a particle diameter of between 1 and 100 nm;
(b) suspending said particles in a first fluid phase to provide a suspension of the particles in said first fluid phase, wherein said first fluid phase comprises a hydrophobic solvent if the particles are hydrophobic, and wherein said first fluid phase comprises a hydrophilic solvent if the particles are hydrophilic;
(c) mixing the suspension formed in step (b) with a second fluid phase in which the first fluid phase is not miscible, thereby providing an emulsion of droplets of the suspension formed in step (b) dispersed in the second fluid phase, wherein said second fluid phase comprises an aqueous phase if the first fluid phase comprises hydrophobic particles suspended in a hydrophobic solvent, and wherein said second fluid phase comprises an hydrophobic phase if the first fluid phase comprises hydrophilic particles suspended in a hydrophilic solvent;
(d) evaporating enough of the hydrophobic or hydrophilic solvent from the emulsion to self-assemble nanoparticles to form microparticles suspended now in the second fluid phase;
(e) providing a polymerizable monomer to the second fluid phase; and
(f) polymerizing the polymerizable monomer to provide a polymer layer on the microparticles.

As indicated above, the general inventive method may be employed in an embodiment in which the first fluid phase comprises a hydrophobic solvent and the second fluid phase comprises an aqueous phase. Alternatively, the general inventive method may be employed in an embodiment in which the first fluid phase comprises a hydrophilic solvent and the said second fluid phase comprises an organic phase.

Additional Aspects of the Invention.

In one aspect of the invention microparticles with optional coating layers are provided. Such particles preferably range in size from 0.01 to 10 µm, although in some embodiments the particles are sized between 0.1 and 10 µm, while in other embodiments the particles are sized between 0.5 and 10 µm. In further embodiments the particles range in size from 0.01 to 5 µm, while in other embodiments the particles are sized between 0.01 and 3 µm. In other embodiments the particles range in size from 0.1 to 5 µm, while in other embodiments the particles range in size from 0.5 to 3 µm.

Whatever size of particle is desired, batches of the particles may be made uniform in size, with a coefficient of variance of less than 40%, preferably less than 20%, more preferably less than 5%, and most preferably less than 2% being obtainable for batches of microparticles made by the disclosed method.

As indicated above, the novel coated magnetic particles prepared by the methods described herein have a magnetic "core" (i.e., the bare nanoparticles without their hydrophobic or hydrophilic coatings, and without a polymer coating) that comprises a significant proportion of the particle's mass. Preferred coated particles have a metal core that comprises in excess of 50%, preferably in excess of 70%, more preferably in excess of 80%, and most preferably in excess of 90%, of the particle's mass.

In one embodiment of the invention the particles[1] have both a bare nanoparticle core in excess of 70% of the particle's mass, and a coefficient of variance (of particle size) of less than 40%. In another embodiment the particles have a bare nanoparticle core in excess of 70% of the particle's mass, and a coefficient of variance of less than 20%, while in another embodiment the particles have both a bare nanoparticle core in excess of 70% of the particle's mass and a coefficient of variance of less than 10%. In another embodiment the particles have a bare nanoparticle core in excess of 70% of the particle's mass and a coefficient of variance (of particle size) of less than 5%.

[1] In the embodiments of the invention in which a coefficient of size variance is identified, the description of the coefficient of variance of the "particles" means the coefficient of variance (size) of a batch or a plurality of individual particles.

In another embodiment of the invention the particles have both a bare nanoparticle core in excess of 80% of the particle's mass and a coefficient of variance (of particle size) of less than 40%, while in another embodiment the particles have a bare nanoparticle core in excess of 80% of the particle's mass and a coefficient of variance of less than 20%. In still another embodiment the particles have both a bare nanoparticle core in excess of 80% of the particle's mass and a coefficient of variance of less than 10%, while in another embodiment the particles have a bare nanoparticle core in excess of 80% of the particle's mass and a coefficient of variance of less than 5%.

In another embodiment of the invention the particles have both a bare nanoparticle core in excess of 90% of the particle's mass and a coefficient of variance (of particle size) of less than 40%, while in another embodiment the particles have a bare nanoparticle core in excess of 90% of the particle's mass and a coefficient of variance of less than 20%. In still another embodiment the particles have a bare nanoparticle core in excess of 90% of the particle's mass and a coefficient of variance of less than 10%, while in another embodiment the particles have a bare nanoparticle core in excess of 90% of the particle's mass and a coefficient of variance of less than 5%.

The coating layers may comprise additional nanoparticles, such as those described in Example 12. Additional polymer layers may also be adsorbed and crosslinked on the surface of the particle to modify the density of the microparticle or provide increase chemical or mechanical stability.

In another aspect of the invention microparticles will be composed on more than one type of nanoparticles. Such microparticles preferably range in size from 0.1 to 10 µm, with microparticles sized between 0.1 and 5 µm being preferred, and microparticles sized between 0.5 and 3 µm being more preferred. Here too, regardless of the size of the individual microparticles, batches of the microparticles may be uniform in size, with a coefficient of variance of less than 40%, preferably less than 20%, more preferably less than 5%, and most preferably less than 2% being obtainable for batches of microparticles made by the disclosed method. These particles can be formed by adding two or more types of nanoparticles to the discontinuous phase in the emulsion, such as those described in Example 11. The only limitation in the types of nanoparticles that can be used is that they must be of similar size and surface energy.

In view of the discussion above, it can be seen that a first embodiment of the invention provides a method of preparing uniform microparticles, comprising:
(a) providing starting nanoparticles having a hydrophobic surface and a particle diameter of between 1 and 100 nm;
(b) suspending said particles in an hydrophobic solvent to provide a suspension of the particles;
(c) mixing the suspension formed in step (b) with a aqueous phase in which the suspension is not miscible, thereby providing an emulsion of droplets of the suspension formed in step (b) dispersed in the aqueous phase;
(d) evaporating enough hydrophobic solvent from the emulsion to assemble microparticles from the nanoparticles, wherein after the evaporation the microparticles become suspended in the aqueous phase;
(e) providing a polymerizable monomer to the aqueous phase; and
(f) polymerizing the polymerizable monomer to provide a polymer layer on the microparticles.

A second embodiment of the invention provides a method as in embodiment 1 wherein the starting nanoparticles comprise a ferromagnetic material.

A third embodiment of the invention provides a method as in embodiment 1 wherein the starting nanoparticles comprise a paramagnetic material.

A fourth embodiment of the invention provides a method as in embodiment 1 wherein the starting nanoparticles comprise a non-magnetic material.

A fifth embodiment of the invention provides a method as in embodiment 1 wherein the starting nanoparticles comprise an alloy.

A sixth embodiment of the invention provides a method as in embodiment 1 wherein the starting nanoparticles comprise magnetite.

A seventh embodiment of the invention provides a method as in embodiment 1 wherein the starting nanoparticles comprise maghemite.

An eighth embodiment of the invention provides a method as in embodiment 1 wherein the starting nanoparticles comprise a material selected from the group consisting of Ni, Co, Mn, Sb, alumina, Cu, Ag, Au, and Mg.

A ninth embodiment of the invention provides a method as in embodiment 1 wherein the starting nanoparticles comprise a polymer.

A tenth embodiment of the invention provides a method as in embodiment 1 wherein the starting nanoparticles comprise one or more types of nanoparticles.

A eleventh embodiment of the invention provides a method as in embodiment 1 wherein the method further includes providing a polymerization initiator to the polymerizable monomer prior to polymerization.

A twelfth embodiment of the invention provides a method as in embodiment 1 wherein the polymerization initiator is provided by adding polymerization initiator to the hydrophobic solvent prior to making emulsion.

A thirteenth embodiment of the invention provides a method as in embodiment 1 wherein the polymerization initiator comprises a ultraviolet light activated initiator.

A fourteenth embodiment of the invention provides a method as in embodiment 13 wherein the polymerization initiator comprises benzophenone.

A fifteenth embodiment of the invention provides a method as in embodiment 11 wherein the polymerization initiator comprises a heat activated initiator.

A sixteenth embodiment of the invention provides a method as in embodiment 1 wherein the method further includes providing a monomer soluble in hydrophobic solvent.

A seventeenth embodiment of the invention provides a method as in embodiment 16 where the monomer soluble in hydrophobic solvent is provided by adding the monomer to the hydrophobic solvent prior to making emulsion.

An eighteenth embodiment of the invention provides a method as in embodiment 16 wherein the monomer comprises styrene.

A nineteenth embodiment of the invention provides a method as in embodiment 1 wherein the method further includes the step of sizing the emulsion formed in step (c) to provide an emulsion wherein at least 95% of the dispersed hydrophobic solvent droplets are sized between 2 and 10 µm.

A twentieth embodiment of the invention provides a method as in embodiment 19 wherein the sizing step comprises passing the emulsion through a membrane.

A twenty-first embodiment of the invention provides a method as in embodiment 20 wherein the membrane comprises pores having a size of 2 to 5 µm.

A twenty-second embodiment of the invention provides a method as in embodiment 1 wherein the hydrophobic solvent and aqueous phase form emulsion by being exposed to shear stress.

A twenty-third embodiment of the invention provides a method as in embodiment 22 wherein the aqueous medium is viscoelastic.

A twenty-fourth embodiment of the invention provides a method as in embodiment 23 wherein the aqueous medium contains 20-30% dextran.

A twenty-fifth embodiment of the invention provides a method as in embodiment 22 wherein the aqueous medium contains carboxymethylcellulose.

A twenty-sixth embodiment of the invention provides a method as in embodiment 22 wherein said hydrophobic solvent and aqueous phase are fed to the shear device in two separate streams.

A twenty-seventh embodiment of the invention provides a method as in embodiment 22 wherein said shear stress is from 800 to 3500 s-1.

A twenty-eighth embodiment of the invention provides a method as in embodiment 22 wherein said shear stress is achieved by using two concentric cylinders rotating to each other.

A twenty-ninth embodiment of the invention provides a method as in embodiment 22 wherein said hydrophobic solvent and aqueous phase are fed to the shear device through the lower port.

A thirtieth embodiment of the invention provides a method as in embodiment 1 wherein the liquid medium of step (b) is an aqueous phase comprising a first surfactant.

A thirty-first embodiment of the invention provides a method as in embodiment 30 wherein said first surfactant comprises SDS.

A thirty-second embodiment of the invention provides a method as in embodiment 30 wherein said method includes the step of washing the self-assembled particles of step (d) to replace the first surfactant with a second surfactant.

A thirty-third embodiment of the invention provides a method as in embodiment 1 wherein said monomer mixture is mixed with sodium hydroxide solution to adjust the pH to 2.8-3.3.

A thirty-fourth embodiment of the invention provides a method as in embodiment 1 wherein said method further includes the step of functionalizing the polymer layer of the microparticles.

A thirty-fifth embodiment of the invention provides a method as in embodiment 34 wherein said functionalizing comprises providing biological receptors to the polymer layer.

A thirty-sixth embodiment of the invention provides a method as in embodiment 35 wherein said biological receptors are linked to the polymer layer through a covalent bond to the carboxylic acids by reacting with 1-ethyl-3-(3-dimethylaminopropyl)-carbodiimide hydrochloride (EDAC).

A thirty-seventh embodiment of the invention provides a method as in embodiment 34 wherein said functionalizing comprises providing nanoparticles to the polymer layer.

A thirty-eighth embodiment of the invention provides a method as in embodiment 37 wherein said nanoparticles are gold nanoparticles.

A thirty-ninth embodiment of the invention provides a method of preparing uniform microparticles, comprising:
  (a) providing starting nanoparticles having either a hydrophobic surface or a hydrophilic surface, wherein said nanoparticles have a particle diameter of between 1 and 100 nm;
  (b) suspending said particles in a first fluid phase to provide a suspension of the particles in said first fluid phase, wherein said first fluid phase comprises a hydrophobic solvent if the particles are hydrophobic, and wherein said first fluid phase comprises a hydrophilic solvent if the particles are hydrophilic;
  (c) mixing the suspension formed in step (b) with a second fluid phase in which the first fluid phase is not miscible, thereby providing an emulsion of droplets of the suspension formed in step (b) dispersed in the second fluid phase, wherein said second fluid phase comprises an aqueous phase if the first fluid phase comprises hydrophobic particles suspended in a hydrophobic solvent, and wherein said second fluid phase comprises an hydrophobic phase if the first fluid phase comprises hydrophilic particles suspended in a hydrophilic solvent;
  (d) evaporating enough of the hydrophobic or hydrophilic solvent from the emulsion to self-assemble nanoparticles to form microparticles suspended now in the second fluid phase;
  (e) providing a polymerizable monomer to the second fluid phase; and
  (f) polymerizing the polymerizable monomer to provide a polymer layer on the microparticles.

A fortieth embodiment of the invention provides a method as in embodiment 39 wherein said first fluid phase comprises a hydrophobic solvent and wherein said second fluid phase comprises an aqueous phase.

A forty-first embodiment of the invention provides a method as in embodiment 39 wherein said first fluid phase comprises a hydrophilic solvent and wherein said second fluid phase comprises an organic phase.

A forty-second embodiment of the invention provides a particle made by the process of embodiment 1.

Further embodiments of the invention provide particles made by any of the processes of embodiments 1 through forty-two.

A forty-fourth embodiment of the invention provides a plurality of particles made by the process of embodiment 1, wherein said plurality of particles comprises particles having a particle size of between 0.01 µm and 10 µm, said particles comprising a paramagnetic core and a polymeric shell, said paramagnetic core comprising at least 70% of the weight of the particle, and wherein the plurality of particles has a coefficient of size variance of less than 40%.

A forty-fifth embodiment of the invention provides a plurality of particles, wherein each particle in said plurality has a particle size of between 0.01 µm and 10 µm, and wherein each particle in said plurality comprises a paramagnetic core and a polymeric shell, wherein said paramagnetic core comprises at least 70% of the weight of the particle, and wherein the plurality of particles has a coefficient of size variance of less than 40%.

A forty-sixth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 70% of the weight of the particle, and wherein the plurality of particles has a coefficient of size variance of less than 40%.

A forty-seventh embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 70% of the weight of the particle, and wherein the plurality of particles has a coefficient of size variance of less than 20%.

A forty-eighth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 70% of the weight of the particle, and wherein the plurality of particles has a coefficient of size variance of less than 10%.

A forty-ninth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 70% of the weight of the particle, and wherein the plurality of particles has a coefficient of size variance of less than 5%.

A fiftieth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 70% of the weight of the particle, and wherein the plurality of particles has a coefficient of size variance of less than 2%.

A fifty-first embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 80% of the weight of the particle, and wherein the plurality of particles has a coefficient of size variance of less than 40%.

A fifty-second embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 80% of the weight of the particle, and wherein the plurality of particles has a coefficient of size variance of less than 20%.

A fifty-third embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 80% of the weight of the particle, and wherein the plurality of particles has a coefficient of size variance of less than 10%.

A fifty-fourth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 80% of the weight of the particle, and wherein the plurality of particles has a coefficient of size variance of less than 5%.

A fifty-fifth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 80% of the weight of the particle, and wherein the plurality of particles has a coefficient of size variance of less than 2%.

A fifty-sixth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 90% of the weight of the particle, and wherein the plurality of particles has a coefficient of size variance of less than 40%.

A fifty-seventh embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 90% of the weight of the particle, and wherein the plurality of particles has a coefficient of size variance of less than 20%.

A fifty-eighth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 90% of the weight of the particle, and wherein the plurality of particles has a coefficient of size variance of less than 10%.

A fifty-ninth embodiment of the invention provides a plurality of particles made by any of the processes of embodiments 1 through forty-two, wherein said plurality of particles comprises particles having a particle size of between 0.01 µm and 10 µm, said particles comprising a paramagnetic core and a polymeric shell, said paramagnetic core comprising at least 90% of the weight of the particle, and wherein the plurality of particles has a coefficient of size variance of less than 5%.

A sixtieth embodiment of the invention provides a plurality of particles made by any of the processes of embodiments 1 through forty-two, wherein said plurality of particles comprises particles having a particle size of between 0.01 μm and 10 μm, said particles comprising a paramagnetic core and a polymeric shell, said paramagnetic core comprising at least 90% of the weight of the particle, and wherein the plurality of particles has a coefficient of size variance of less than 2%.

EXAMPLES

Reference will now be made to specific examples using the processes described above. It is to be understood that the examples are provided to more completely describe preferred embodiments, and that no limitation to the scope of the invention is intended thereby.

Example 1

Formation of Polymer Coated Microparticles

The general procedure to produce microparticles is illustrated in FIG. 1.

(a) Formation of Iron Oxide Nanoparticle

The iron oxide nanoparticles were prepared by co-precipitating ferric chloride and ferrous chloride in deoxygenated water under alkaline conditions. Ammonium hydroxide was rapidly added to the solution with vigorous stirring and the resulting reaction mixture heated to about 70° C., and maintained at that temperature with continued stirring for about 30 minutes to give a black slurry of magnetic nanoparticles. The slurry was washed first with water and then with 18% (v/v) perchloric acid. The resulting nanoparticles were dialyzed using 12,000-14,000 Da tubing (available from Spectrum, Rancho Dominguez, Calif.) to remove any remaining acid. The magnetic nanoparticles were filtered with a 1 μm Nuclepore polycarbonate membrane (available from Whatman, Florham Park, N.J.).

(b) Making the Particle's Surface Hydrophobic

The magnetic nanoparticles were hydrophobized by suspending the particles in a 16% oleic acid solution for 20 minutes with stirring. Excess oleic acid was removed with an ethanol rinse and the particles re-suspended in hexane to give an approximate 5% w/v concentration of magnetic nanoparticles.

(c) Locating UV Initiator on the Particle's Surface, Refining the Initially Formed Emulsion and Preparing to Form Outer Polymer Coating Sufficient benzophenone was added to the hexane slurry to give a 100 μM concentration of benzophenone in the slurry. Four parts of an aqueous solution of sodium dodecyl sulfate (SDS) (1%) were added to one part of the hexane slurry and the mixture was vortexed to give a crude oil-in-water emulsion. The crude emulsion was forced through a 2 or 5 μm Isopore membrane (available from Millipore, Billerica, Mass.) in an extruder (available from Northern Lipids, Vancouver Canada) at a pressure of from about 5 to about 10 psi to refine the size of the crude emulsion. The resulting emulsion was further diluted with a 40 mM aqueous SDS solution (1:27 ratio) and the hexane was allowed to evaporate at room temperature. The result was micron size magnetic particles suspended in SDS solution.

(d) Replacing SDS on Particle's Surface with Polymerizable Surfactant (RN-10)

The SDS on the microparticle's surface was replaced with nonylphenoxypropenyl polyethylate alcohol (Noigen®, RN-10, marketed by Dai-Ichi Kogyo Seiyaku Co., Ltd. of Japan) by rinsing the particle three times with a 1% RN-10 solution in water.

(e) Forming Outer Polymer Coating to the Microparticles

A portion of the resulting microparticles was combined with the individual monomer mixtures shown in Table I, agitated and exposed to a 20 mW/cm² UV light for about 10 minutes to give a viscous mixture. The mixture was diluted with methanol and particles were collected with a permanent magnet, rinsed with water and stored at about 4° C.

TABLE I

| Sample | Acrylic Acid (g) | RN-10 (g) | Water (g) | CCC* (mM) | AA:RN-10 |
|---|---|---|---|---|---|
| 1 | 6.4 | 1.6 | 32 | 157 | 23:1 |
| 2 | 4.8 | 3.2 | 32 | 118 | 22:1 |
| 3 | 3.2 | 4.8 | 32 | 76 | 20:1 |
| 4 | 1.6 | 6.4 | 32 | 26 | 11:1 |

*CCC is the Critical Coagulation Concentration

Figure 3:
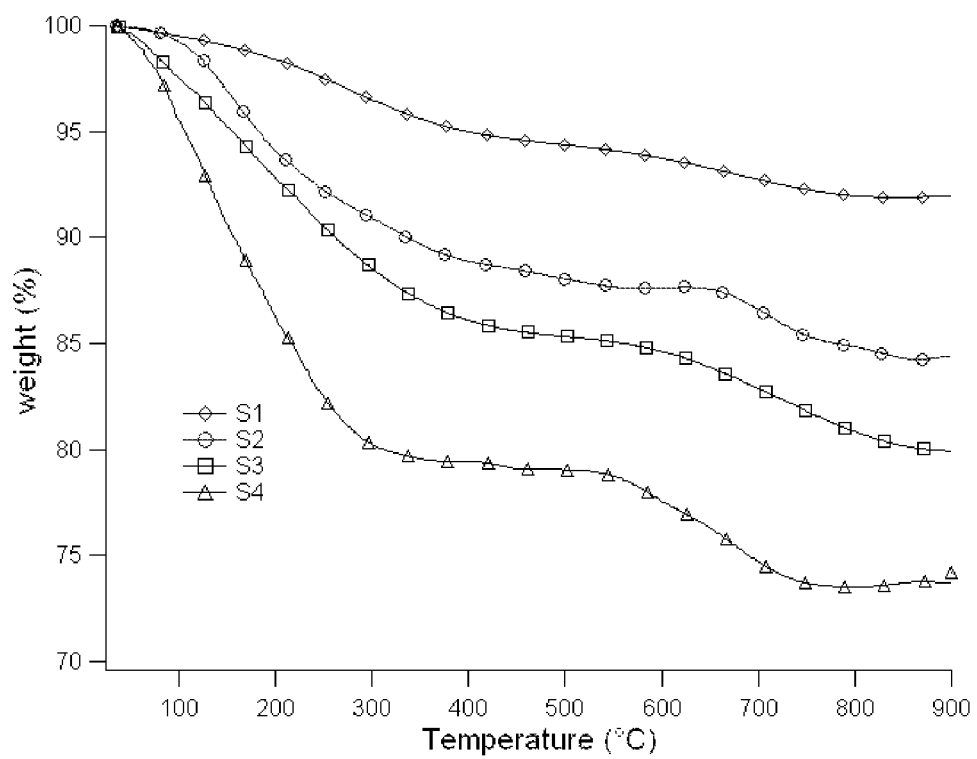
FIG. 3 shows the temperature programmed decomposition profiles of the microparticles.

The coated microparticles described above generally had an average particle diameter of less than about 2 μm. Thermal gravity analysis (TGA) studies demonstrated a mass loss of about 8% for sample 1 suggesting that the organic materials represented about 8% of the particle's mass and magnetic core represented about 92% of the particle's mass (FIG. 3). Sample 4 had the largest mass loss, which counts for 27% of the total particle weight. The remaining weight for sample 4 was about 73%. The density of the coated magnetic microparticles produced was about 2.6 g/cm³, which is considerably higher than the normal 1 to 1.5 g/cm³ for conventional magnetic particles comprising magnetic nanoparticles within a polymer particle. This is indicative of the greater than normal magnetic material content of the coated microparticles. The colloidal stability of the coated metal nanoparticles was examined in various concentrations of sodium chloride. The critical coagulation concentrations (CCC) were determined and are provided in Table I. Magnetization measurements were performed on the Sample 1 indicating a saturation magnetization of about 45.9 emu/g.

Figure 4:
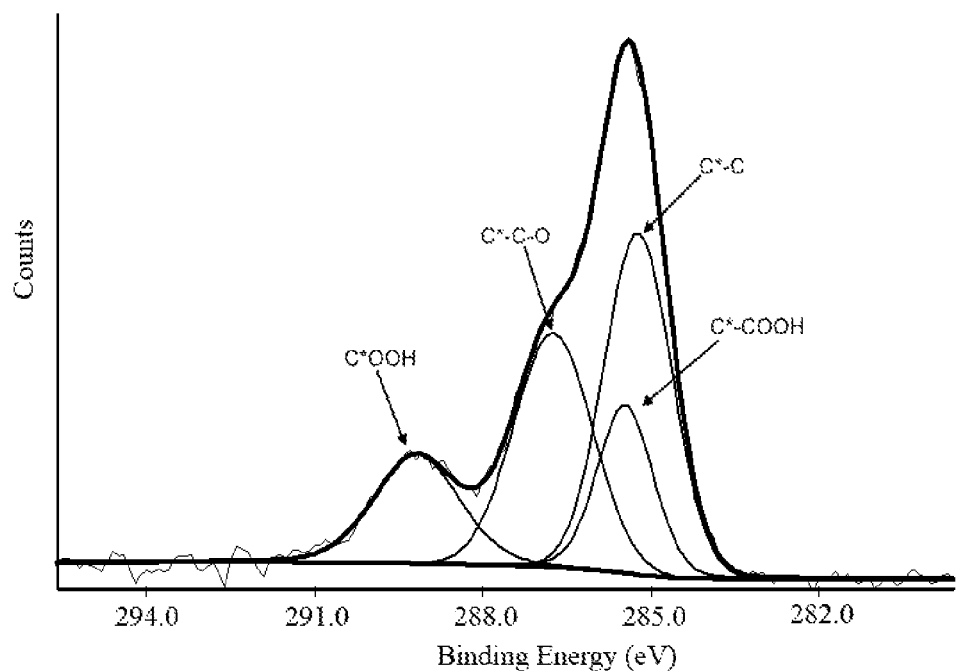
FIG. 4 shows the x-ray photoelectron spectrum of the microparticles produced by sample 4 in Example 1.

The coated particles were analyzed using x-ray photoelectron spectroscopy (XPS) to determine the molar ratio of acrylic acid (AA) to RN-10. The XPS spectrum of sample 4 is shown in FIG. 4. The ratios of monomers in the surface layer of the particles are provided in the last column of Table I.

Similarly coated particles were formed according to this general procedure with acrylamide with and without the replacement of the SDS with RN-10 prior to polymerization to give similarly coated microparticles. Other water-soluble monomers can be similarly utilized both with and instead of the acrylic acid and water soluble cross-linking agents such as di- and tri-acrylate esters of diols, triols or other polyols can similarly be added to the monomer mixture.

Although the micron size magnetic core utilized in this example was an agglomeration of smaller magnetic nanoparticles, similar nanoparticles derived from other material can be coated with the procedure described above. Finally, the UV initiator, benzophenone, can be replaced with a generally water insoluble heat sensitive polymerization initiator and the polymerization can be carried out by heating the mixture to a temperature of not more than about 75° C.

Example 2

Formation of Hydrophobic Magnetite Nanoparticles Using One-step Synthesis Chemistry A 250 ml three neck flask was charged with 12.0 g $FeCl_2.4H_2O$ and 24.3 g $FeCl_3.6H_2O$ in 50 ml deoxygenated water under $N_2$ atmosphere. Rapidly add 40 ml ammonium hydroxide. The solution was heated to 70° C. for 30 min. Five milliliter oleic acid was added to the solution and heated for another 30 min. The black slur was washed three times with water, 20% perchloric acid and ethanol. The slur was suspended into hexane at 5% (w/v) and stored at 4° C. The magnetization measurement showed that the particle had the saturation magnetization of 56 emu/g.

Example 3

Manipulation of Benzophenone Concentration

The method of example 1 was repeated with three different benzophenone concentrations, 1 μM, 10 μM, and 100 μM. The coated particles prepared with a 1 μM level of benzophenone were gel-like. The coated particles prepared with a 10 μM level of benzophenone were less gel-like, but displayed a strong tendency to adhere to a glass surface. The coated particles prepared with a 100 μM level of benzophenone were discrete and easily collected by diluting with methanol and appeared stable.

Example 4

Figure 5:
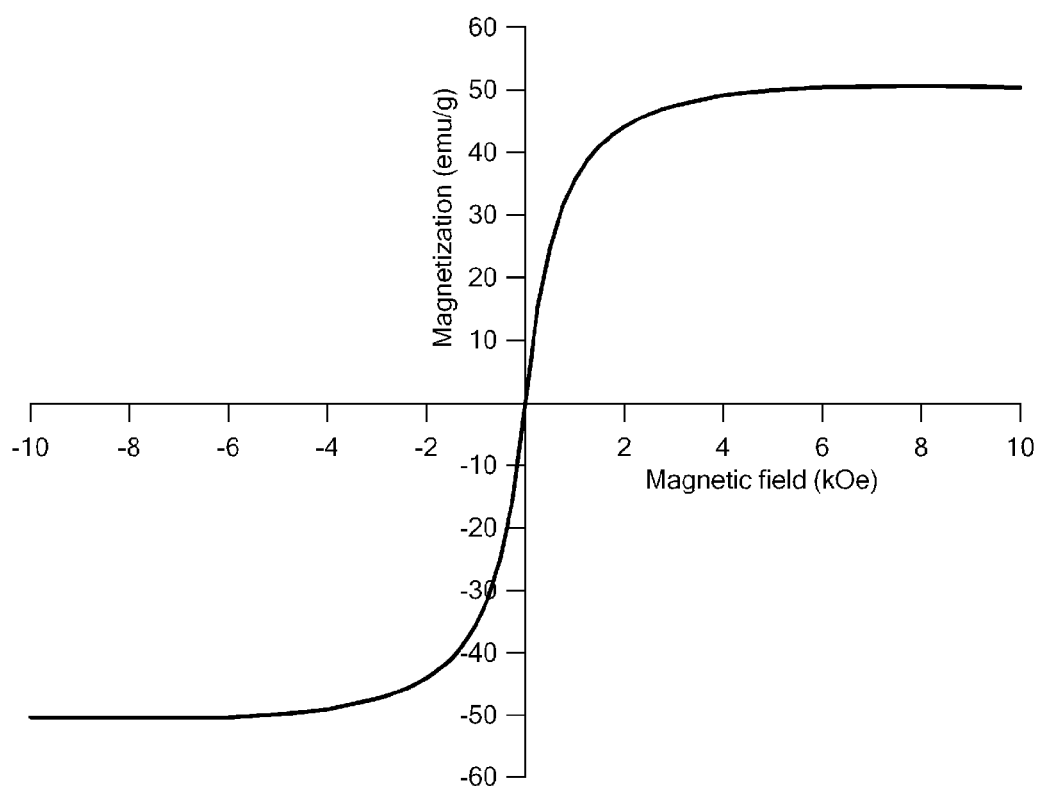
FIG. 5 shows the magnetization curve of the magnetic microparticles.

Formation of Hydrophobic Magnetite Nanoparticles Using One-step Synthesis Chemistry The method of example 1 was repeated with the particles prepared in example 2. The magnetization measurement showed that the particle had the saturation magnetization up to 50.6 emu/g as indicated in FIG. 5.

Example 5

Refinement of the Emulsion Size by Shear Stress

Figure 6:
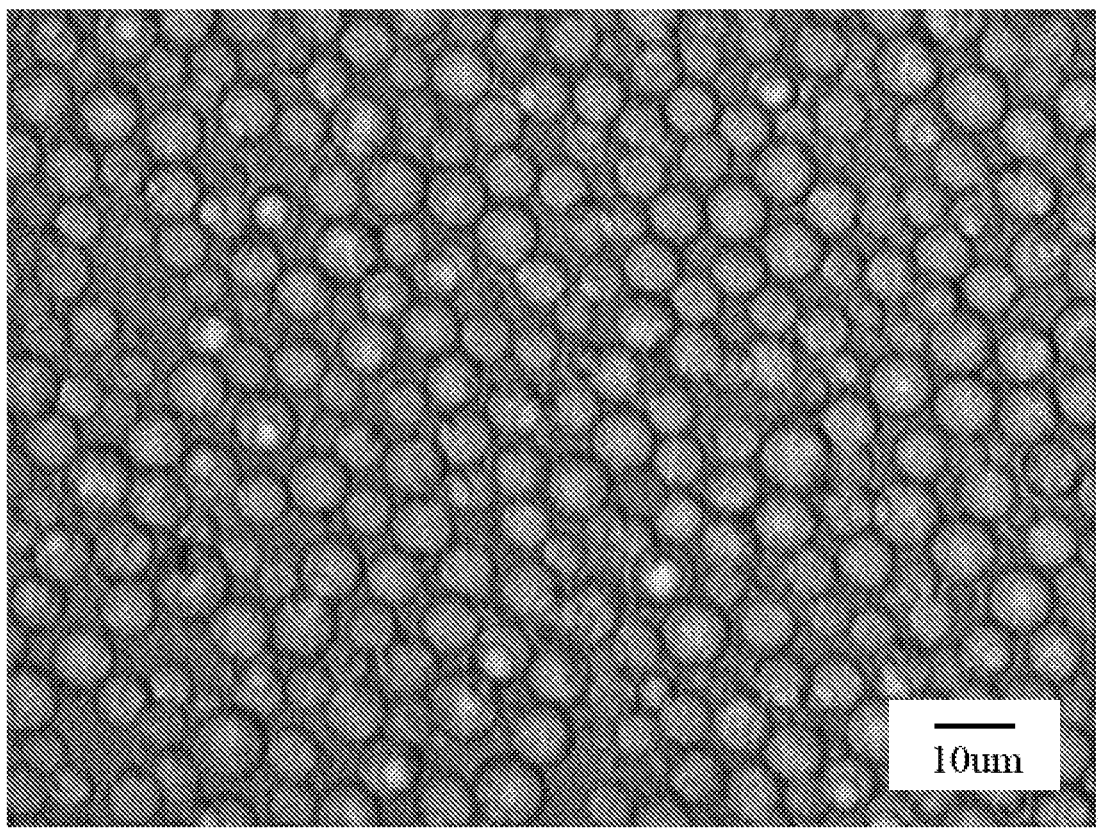
FIG. 6 shows the emulsion produced by shear stress.
Figure 7:
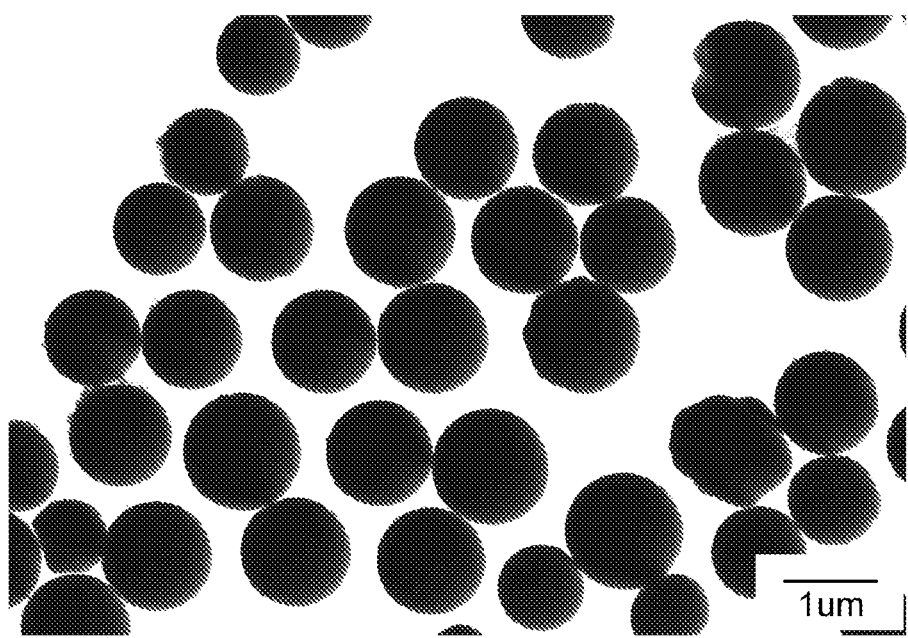
FIG. 7 shows the TEM image of the particles consisting of iron oxide nanoparticles.
Figure 8:
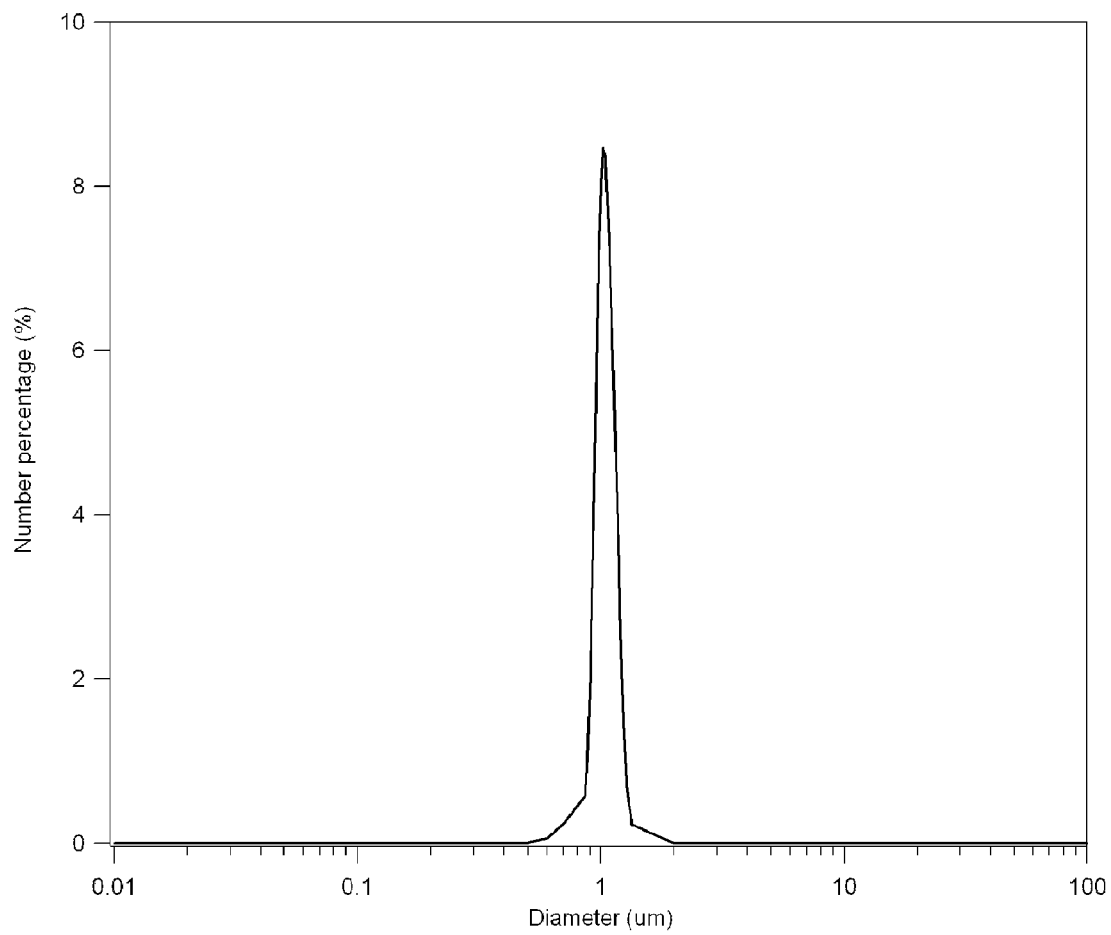
FIG. 8 shows the particle size distribution obtained with 30% dextran solution.

The nanoparticles prepared in Example 2 were adjusted to the solid content of 0.78% by adding hexane. Benzophenone was added to the concentration of 100 μM. The aqueous solution contained 1% SDS and 30% dextran (MW 100-200K). The hexane solution and aqueous solution were fed into the shear device at the same flow rate using two separate syringes. The solution was subject to a shear rate of 840 $s^{-1}$. The monodisperse emulsion was collected in 0.1% SDS solution (FIG. 6). The hexane was allowed to evaporate. The particles were resuspended in 10% RN-10 and 10% acrylic acid solution. The polymerization was carried out by exposing the particles to 20 $mW/cm^2$ UV light for about 10 minutes. The microparticles were centrifuged at 100 g for 10 times. Each time the upper solution was discarded and the particles were resuspended in water. The final particle showed the diameter around 1 um and coefficient of variance less than 10% as indicated by the FIG. 7 and 8. The zeta potential of the particle was −1.9 mV.

Example 6

Alternative Refinement of the Emulsion Size by Shear Stress

The operating procedure in this example is identical to that in Example 5 except 20% dextran was used and the shear stress was adjusted to 3450 $s^{-1}$.

Example 7

Second Alternative Refinement of the Emulsion Size by Shear Stress

The operating procedure in this example is identical to that in Example 5 except 3.3% carboxymethylcellulose (Cellogen®, HP-8A, marketed by Dai-Ichi Kogyo Seiyaku Co., Ltd. of Japan) was used.

Example 8

Adding Hydrophobic Monomers and Cross-linkers to the Hydrophobic Phase

The operating procedure in this example is identical to that in Example 5 except that in addition to benzophenone, styrene was added to hexane at 1.9M and divinylbenzene was added to hexane at 0.46M prior to the formation of emulsion. The final particle showed higher stability when exposed to acidic solutions.

Example 9

Adjustment of the pH of the Monomer

The method of Example 5 was repeated with the pH of the monomer mixture being adjusted by sodium hydroxide solution to 3.1. The resulting microparticles were well separated in aqueous solution and the zeta potential of the particle was −2.88 mV. Further testing showed the optimal pH is 2.8-3.3.

Example 10

Formation of Acrylamide Coated Microparticles

The operating procedure in this example is identical to that in Example 5 except 7% acrylamide was used to replace acrylic acid.

Example 11

Assembly of Microparticles From Gold and Iron-oxide Nanoparticles

Figure 9:
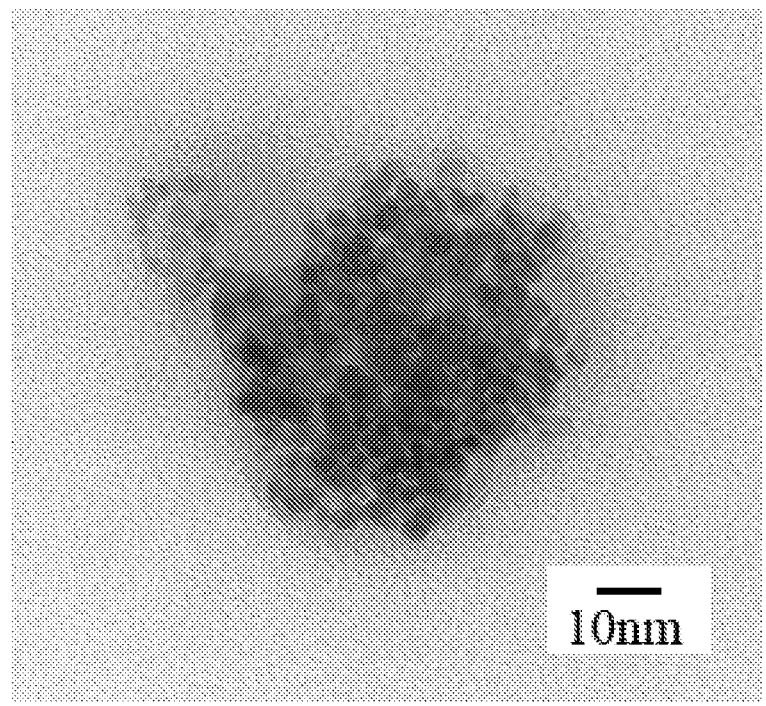
FIG. 9 shows the TEM image of the particles consisting of iron oxide and gold nanoparticles.

The commercially available 10 nm Au nanoparticle (available from BBInternational, Golden Gate, Ty Glas Ave., Cardiff CF14 5DX UK) was concentrated 10 times using centrifugation. A glass vial was charged with 0.5 ml of 1 mM dodecane thiol ethanol solution, 1 ml concentrated Au nanoparticle in water and 1 ml of 10 mM dodecane thiol hexane solution. The mixture was rotated for 24 hr. The modified Au nanoparticles became purple and moved into the hexane layer. The hexane layer was collected and stored in refrigerator until use. The magnetite particle prepared in example 2 was diluted 10 times in hexane and mixed with the modified Au nanoparticles at a 1:1 ratio. The 1 ml particle mixture was added into 5 ml 1% SDS solution and transformed into an emulsion by passing through a 200 nm membrane. The hexane was allowed to evaporate overnight. The particles were observed under transmission electron microscope. FIG. 9 showed that the Au and magnetite nanoparticles mixed together and assembled into micron size particles.

Example 12

Outside Decoration of Iron-oxide Microparticle with Au Nanoparticles

Figure 10:
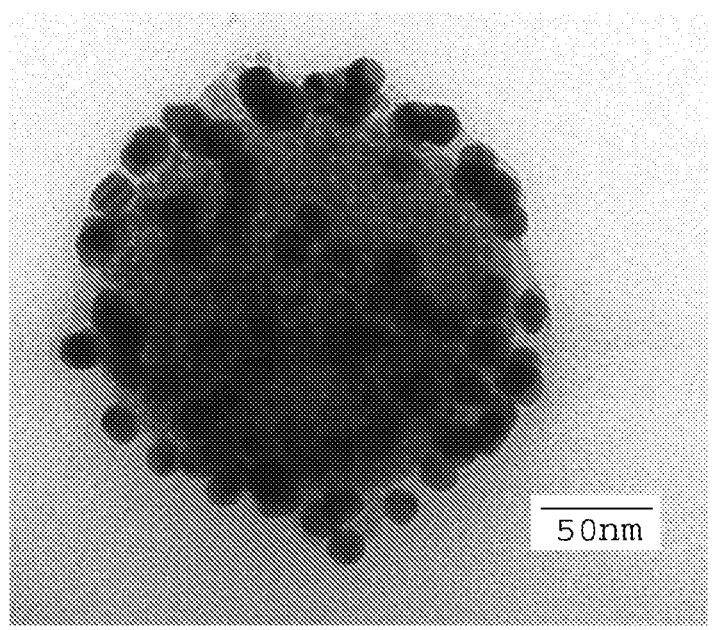
FIG. 10 shows the TEM image of the magnetic particles with outside binding of gold nanoparticles.
Figure 11:
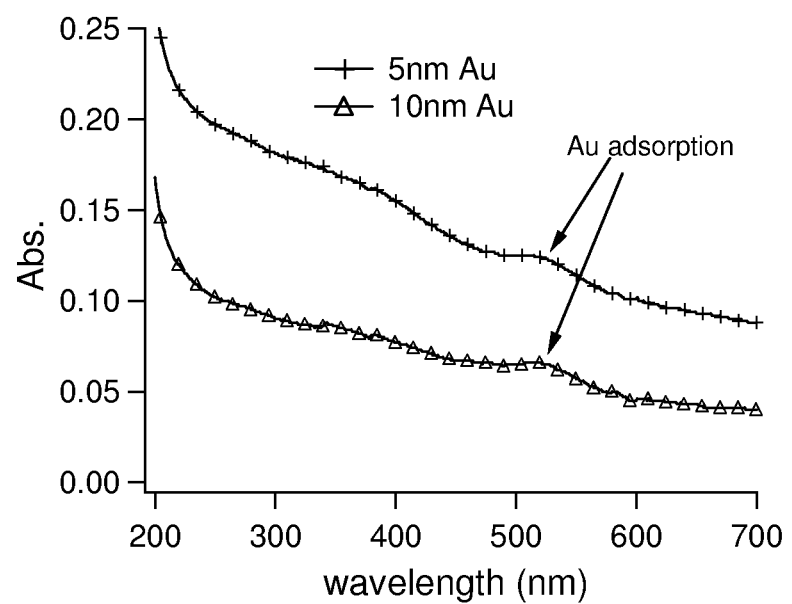
FIG. 11 is a UV-Vis spectrum of Au nanoparticle decorated magnetic particles, showing the adsorption peak of the magnetic particles modified with 5 nm Au and 10 nm Au nanoparticle, respectively.

A glass vial was charged with 0.1 ml magnetite nanoparticles prepared in Example 2, 0.9 ml hexane and 0.5 ml 1 mM benzophenone. The solution was well mixed before 5 ml 1% SDS solution was added. The mixture was shaken by hand to make crude emulsions. The crude emulsion was passed through a 200 nm membrane (Whatman, Florham Park, N.J.) using a syringe. The hexane was allowed to evaporate for 12 hr at room temperature. The resulting particles were rinsed with 1% RN-10 solution three times. The particles were mixed with 5 ml 1% RN-10 and 2 ml of 5M acrylamide. The mixture was exposed to 20 mW/cm$^2$ UV light for about 10 minutes. The particles were separated using a magnet, rinsed with water, and resuspended in water. The 20 nm Au nanoparticles (BBInternational, Golden Gate, Ty Glas Ave., Cardiff CF14 5DX UK) were concentrated 3 times using centrifugation. About 1 ml of the Au nanoparticles was mixed with 0.1 ml of amine modified magnetic particles. The mixture was rotated overnight. The magnetic particles were collected with magnet, rinsed with water, and re-suspended in 1 ml water. The Au modified magnetic particles were examined using TEM and UV-Vis spectrophotometer. The TEM showed that the magnetic particles were decorated with Au nanoparticles on the outside (FIG. 10). The UV-Vis spectrophotometry measurement showed the signature adsorption peak from the attached Au nanoparticles (FIG. 11).

Example 13

Modification with Mouse Anti-M13

Figure 12:
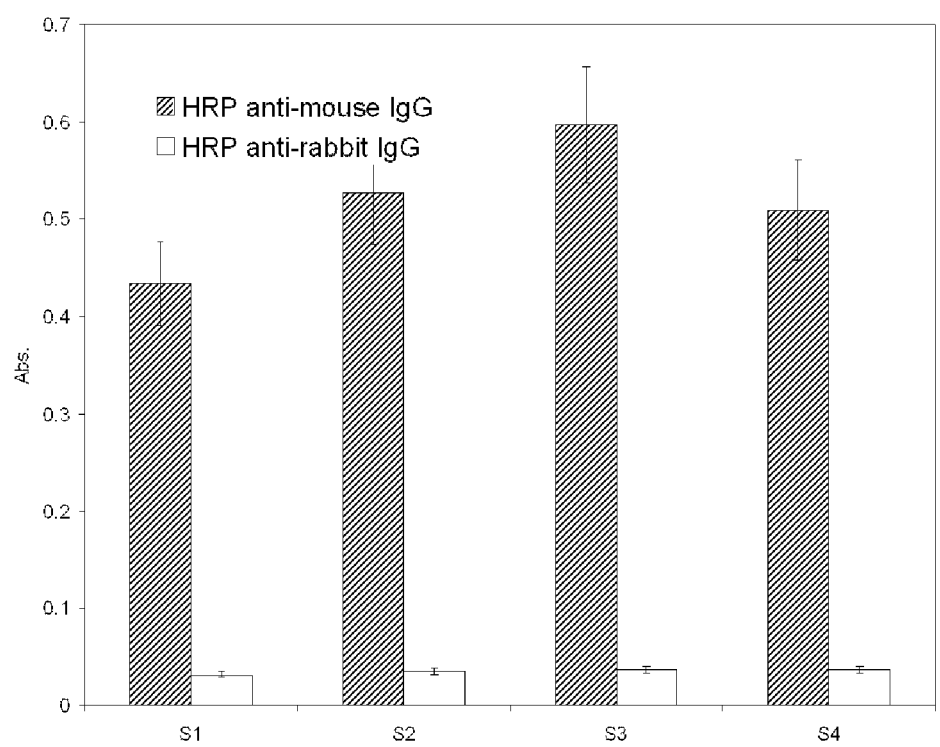
FIG. 12 is a calorimetric signal produced by the antibody-HRP conjugates on the microparticles prepared using the reaction conditions described in Table 1.

The microparticles prepared in Example 1 were modified with mouse anti-M13 IgG (available from Amersham Pharmacia, Piscataway, N.J.) using 1-ethyl-3-(3-dimethylaminopropyl)-carbodiimide hydrochloride (EDAC) coupling chemistry. A mixture containing 200 µl of particles, 600 µl water, 50 µl of 500 mM 2-(morpholino)ethanesulfonic acid (MES, available from Sigma) having a pH of 6.1 and 100 µl of the antibody were sonicated at low power in an ice bath. After about 15 minutes, 290 µl of EDAC (available from Sigma) was added to the mixture and sonication continued for an additional 15 minutes. The resulting mixture was incubated on a rotation wheel for about 1 hour after which the particles were washed three times with 12 mM phosphate buffered saline solution (PBS). After washing, horseradish peroxidase (HRP) anti-mouse IgG conjugate (available from KPL, Gaithersburg, Md.) was added at 0.01 mg/ml and HRP anti-rabbit IgG was added to the control groups. After incubating the mixtures for 1 hour, the particles were washed three times with PBS solution. The presence of HRP was detected by adding 1 mg/ml of 2,2'Azinobis[3-ethylbenzothiazoline-6-sulfonic acid]diammonium salt (ABTS) and determining the absorbance of the green end product at about 410 nm. The relative concentrations of HRP were proportional to the absorbance determined. FIG. 12 illustrates the strong specific absorbance of the HRP anti-mouse IgG and the much weaker nonspecific absorbance of the HRP anti-rabbit IgG by the coated microparticles.

While applicant's invention has been described with reference to specific embodiments both above and in the attachments provided, it will be understood that modifications and alterations in the embodiments disclosed may be made by those practiced in the art without departing from the spirit and scope of the invention. All such modifications and alterations are intended to be covered. In addition, all publications cited herein are hereby incorporated by reference in their entirety as if each had been individually incorporated by reference and fully set forth.

What is claimed is:

1. A method of preparing polymer coated microparticles, comprising:
   (a) providing starting nanoparticles having a hydrophobic surface and a particle diameter of between 1 and 100 nm, wherein the starting nanoparticles comprise at least one magnetic material;
   (b) suspending said starting nanoparticles in an hydrophobic solvent to provide a suspension of the particles;
   (c) mixing the suspension formed in step (b) and an aqueous phase in which the suspension is not miscible, thereby providing an emulsion of droplets of the suspension formed in step (b) dispersed in the aqueous phase,
   (c-1) thereafter sizing the emulsion formed in step (c) to provide an emulsion wherein the dispersed hydrophobic solvent droplets are sized between 2 and 20 µm;
   (d) evaporating enough hydrophobic solvent from the emulsion to assemble microparticles from the nanoparticles, wherein after the evaporation the microparticles become suspended in the aqueous phase;
   (e) providing a polymerizable monomer to the aqueous phase; and
   (f) polymerizing the polymerizable monomer to provide a polymer layer on the microparticles;
   wherein the polymer coated microparticles have a metal core that is greater than 50% of the mass of the mass of the polymer coated microparticles, wherein the metal core is the bare nanoparticles without both their hydrophobic coating and their polymer coating; and
   wherein the polymer coated microparticles have a size ranging from 0.01 to 10 µm.

2. The method of claim 1 wherein said starting nanoparticles comprise a paramagnetic material.

3. The method of claim 1 wherein said starting nanoparticles comprise magnetite or maghemite.

4. The method of claim 1 wherein said starting nanoparticles comprise a material selected from the group consisting of Ni, Co, Mn, Sb, alumina, Cu, Ag, Au, Mg, and polymers.

5. The method of claim 1 wherein said method further includes providing a polymerization initiator to the polymerizable monomer prior to polymerization.

6. The method of claim 5 wherein said polymerization initiator is provided by adding said polymerization initiator to the hydrophobic solvent prior to making emulsion.

7. The method of claim 5 wherein said polymerization initiator comprises an ultraviolet light activated initiator.

8. The method of claim 7 wherein said polymerization initiator comprises benzophenone.

9. The method of claim 1 wherein said method further includes providing a monomer soluble in hydrophobic solvent.

10. The method of claim 9 wherein the monomer soluble in hydrophobic solvent is provided by adding the monomer to the hydrophobic solvent prior to making emulsion.

11. The method of claim 10 wherein said monomer comprises styrene.

12. The method of claim 1 wherein step (c-1) makes at least 95% of the dispersed hydrophobic solvent droplets sized between 2 and 10 μm.

13. The method of claim 1 wherein said sizing step comprises passing the emulsion through a membrane.

14. The method of claim 13 wherein said membrane comprises pores having a size of 2 to 5 μm.

15. The method of claim 1 wherein said sizing step comprises exposing said hydrophobic solvent and aqueous phase to shear stress to form the emulsion wherein at least 95% of the dispersed hydrophobic solvent droplets are sized between 2 and 10 μm, and wherein the aqueous phase is viscoelastic.

16. The method of claim 15 wherein the aqueous medium contains 20-30% dextran.

17. The method of claim 15 wherein the aqueous medium contains carboxymethylcellulose.

18. The method of claim 15 wherein said shear stress is from 800 to $3500s^{-1}$.

19. The method of claim 1 wherein the liquid medium of step (b) is an aqueous phase comprising a first surfactant.

20. The method of claim 19 wherein said first surfactant comprises Sodium Dodecyl Sulfate (SDS).

21. The method of claim 1 wherein said method includes the step of washing the assembled particles of step (d) to replace the first surfactant with a second surfactant.

22. The method of claim 1 wherein said monomer mixture is mixed with sodium hydroxide solution to adjust the pH to 2.8-3.3.

23. The method of claim 1 wherein said method further includes the step of functionalizing the polymer layer of the microparticles.

24. The method of claim 23 wherein said functionalizing comprises providing biological receptors to the polymer layer.

25. The method of claim 24 wherein said biological receptors comprise carboxylic acid groups and are linked to the polymer layer through a covalent bond to the carboxylic acids by reacting with 1-ethyl-3-(3-dimethylaminopropyl)-carbodiimide hydrochloride (EDAC).

26. The method of claim 23 wherein said functionalizing comprises providing nanoparticles to the polymer layer.

27. The method of claim 26 wherein said nanoparticles are gold nanoparticles.

28. A method of preparing polymer coated microparticles, comprising:
(a) providing starting nanoparticles having either a hydrophobic surface or a hydrophilic surface, wherein said nanoparticles have a particle diameter of between 1 and 100 nm, wherein the starting nanoparticles comprise at least one magnetic material;
(b) suspending said starting nanoparticles in a first fluid phase to provide a suspension of the particles in said first fluid phase, wherein said first fluid phase comprises a hydrophobic solvent if the starting nanoparticles are hydrophobic, and wherein said first fluid phase comprises a hydrophilic solvent if the starting nanoparticles are hydrophilic;
(c) mixing the suspension formed in step (b) with a second fluid phase in which the first fluid phase is not miscible, thereby providing an emulsion of droplets of the suspension formed in step (b) dispersed in the second fluid phase, wherein said second fluid phase comprises an aqueous phase if the first fluid phase comprises hydrophobic starting nanoparticles suspended in a hydrophobic solvent, and wherein said second fluid phase comprises an organic phase if the first fluid phase comprises hydrophilic starting nanoparticles suspended in a hydrophilic solvent;
(c-1) thereafter sizing the emulsion formed in step (c) to provide an emulsion wherein the dispersed hydrophobic solvent droplets or organic phase droplets are sized between 2 and 20 μm;
(d) evaporating enough of the hydrophobic or hydrophilic solvent from the emulsion to self-assemble nanoparticles to form microparticles suspended in the second fluid phase;
(e) providing a polymerizable monomer to the second fluid phase; and
(f) polymerizing the polymerizable monomer to provide a polymer layer on the microparticles;
wherein the polymer coated microparticles have a metal core that is greater than 50% of the mass of the mass of the polymer coated microparticles, wherein the metal core is the bare nanoparticles without both their hydrophobic coating and their polymer coating; and
wherein the polymer coated microparticles have a size ranging from 0.01 to 10 μm.

29. The method of claim 28 wherein said first fluid phase comprises a hydrophilic solvent and wherein said second fluid phase comprises an organic phase.

30. The method of claim 28 wherein the polymer coated microparticles have a metal core that is greater than 70% of the mass of the mass of the polymer coated microparticles.

31. The method of claim 28 wherein step (c-1) makes at least 95% of the dispersed hydrophobic solvent droplets or organic phase droplets sized between 2 and 10 μm.

32. The method of claim 1 wherein the polymer coated microparticles have a metal core that is greater than 70% of the mass of the mass of the polymer coated microparticles.

33. The method of claim 1 wherein the polymer coated microparticles have a metal core that is greater than 90% of the mass of the mass of the polymer coated microparticles.

* * * * *